United States Patent [19]

Campbell

[11] Patent Number: 5,061,249

[45] Date of Patent: Oct. 29, 1991

[54] HYPODERMIC INJECTION DEVICE

[76] Inventor: William P. Campbell, 3310 Rowland Place, Washington, D.C. 20008

[21] Appl. No.: 494,664

[22] Filed: Mar. 16, 1990

[51] Int. Cl.⁵ .............................................. A61M 5/32
[52] U.S. Cl. .................................... 604/195; 604/110
[58] Field of Search ............... 604/195, 263, 187, 110, 604/272, 243, 218

[56] References Cited

U.S. PATENT DOCUMENTS

| | | | |
|---|---|---|---|
| 2,840,075 | 6/1955 | Dann et al. | 604/900 X |
| 4,692,156 | 9/1987 | Haller | 604/110 X |
| 4,803,370 | 2/1989 | Haber et al. | 604/195 |
| 4,944,723 | 7/1990 | Haber et al. | 604/195 |

Primary Examiner—John D. Yasko
Attorney, Agent, or Firm—Antonelli, Terry Stout & Kraus

[57] ABSTRACT

Disclosed is a hypodermic injection device wherein the needle can be retracted into the reservoir chamber, after use, for disposal. The device includes a plunger having a needle-retention chamber in the end of the plunger closest to the needle structure. The end portion of the needle can be resilient, and shaped, such that the end of the needle can be retained in the needle-retention chamber when the plunger reaches the end of its stroke toward the needle. Other structures for ensuring retention of the needle is the needle-retention chamber are also disclosed. Also disclosed is structure for ensuring that the needle cannot be relocated for re-use, once it has been withdrawn into the reservoir chamber, and structure avoiding accidental retention of the needle in the needle-retention chamber.

22 Claims, 9 Drawing Sheets

HYPODERMIC INJECTION DEVICE

BACKGROUND OF THE INVENTION

The present invention is directed to a hypodermic injection device (e.g., a hypodermic syringe). More particularly, the present invention is directed to such a hypodermic injection device wherein, after use of the needle for injection, the needle can be withdrawn into the hypodermic reservoir chamber (that is, the chamber that held the injectable material) so that the needle is no longer exposed after use.

An increasing problem for health care professionals is on-the-job contamination by used hypodermic needles. Because of the hundreds of needles used in hospital and office settings each week, it has been estimated that a puncture wound from used needles occurs as often as once every one or two weeks per health care worker. With the outbreak of AIDS and other deadly bloodborne diseases, this has become an area of increasing concern. Likewise, the sharing of needles by drug abusers, and even sharing in the clinical environment, represents a real threat to the public.

Various prior devices have been developed in order to withdraw the hypodermic needle into the hypodermic reservoir chamber after use, to completely isolate the needle immediately after the patient is injected and to allow the hypodermic reservoir chamber to be subsequently discarded with the needle therein. One prior device is shown in U.S. Pat. No. 4,813,936. This patent describes a needle assembly for the hypodermic syringe including a hollow needle with an inner end inside the hypodermic reservoir chamber which held the injectable material, the reservoir chamber including a passage through which the needle extends and is slidable, the needle having stop means limiting outward movement of the needle relative to the reservoir chamber but not limiting inward movement of the needle as the needle is withdrawn into the reservoir chamber. This patent discloses that the plunger used to cause emptying of the injectable material that was held within the hypodermic reservoir chamber, slidably mounted within such chamber, has an end closest to the needle that is made of a plug of relatively soft material, while the end of the needle within the chamber includes structure (such as barbs) which can enter the soft material. Upon use, the plunger is depressed such that the end of the needle within the chamber pierces the end of the plug and is retained therein due to the plurality of barbs. Once engagement of the needle and plug has occurred, the plunger can then be withdrawn whereby the needle engaged to the plug is also withdrawn into the reservoir chamber.

However, the design shown in U.S. Pat. No. 4,813,936 requires a relatively complex needle structure, undesirably increasing the cost of the needle and, accordingly, the overall cost of the hypodermic syringe.

U.S. Pat. No. 4,826,484, the contents of which are incorporated herein by reference, also discloses a syringe having a retractable needle, the syringe including a cylinder or barrel having a closed distal end and an open proximal end, with a first end of the needle projecting outwardly from the distal end of the cylinder, and by which a fluid may be injected; a second end of the needle extends into the interior of the cylinder, and terminates at a relatively large needle catch. The syringe includes a plunger which is adapted for reciprocal and axial movement through the syringe cylinder, the plunger including a detachable connection of an elongated stem to a sealing and locking assembly. An elastomeric seal is formed at one end of the sealing and locking assembly, and functions as a plunger head when the plunger is moved axially through the cylinder during a fluid injection procedure. The seal is mounted around a plurality of flexible legs which define a needle capturing receptacle therebetween. When the plunger is moved through the syringe cylinder at the conclusion of a fluid injection procedure, the seal is pressed against the most distal aspect of the cylinder, such that the needle capturing receptacle is advanced axially into engagement with the needle catch; the needle catch is thereby received by the needle capturing receptacle, and upon withdrawal of the plunger back into the cylinder the needle is also withdrawn into the cylinder.

The needle structure disclosed in U.S. Pat. No. 4,826,484 requires a needle catch at the end of the needle, such needle catch being an enlarged structure formed at the end of the needle within the syringe cylinder, and also requires a relatively complex locking assembly for the plunger, including a plurality of flexible legs for retaining the needle in the plunger. Such relatively complex structure for both the needle and plunger increases the complexity of manufacturing the syringe, and increases the cost thereof.

U.S. Pat. No. 4,838,870 also discloses a syringe having a retractable needle, with the end of the needle having an enlarged portion at the end which can be captured by a needle capturing receptacle in the end of the plunger, similar to the structure described in the previously discussed U.S. Pat. No. 4,826,484. U.S. Pat. No. 4,838,870 further discloses that the needle also includes a further thickened portion, which is larger than the diameter of the hole in the syringe cylinder through which the needle extends out of the cylinder, for preventing movement of the needle in a direction out of the cylinder. U.S. Pat. No. 4,838,870 also discloses that the needle and support therefor can be independent of the syringe cylinder and removably attached thereto, so that different needles (for example, having different needle sizes) can be used with the same syringe cylinder.

U.S. Pat. No. 4,804,370 discloses a syringe having a retractable needle, wherein the needle has a thickened portion at the end thereof adapted to be retained in a needle capturing receptacle at the end of the plunger, similar to the structure previously described in connection with U.S. Pat. No. 4,826,484. U.S. Pat. No. 4,804,370 further discloses that the flexible legs of the needle capturing receptacle should have an offset configuration so that when the used needle is withdrawn into the syringe cylinder, the used needle will be canted or slanted relative to the vertical, whereby the needle is misaligned with respect to the opening in the end of the cylinder. Due to such misalignment, the needle cannot be repositioned so as to extend outside the cylinder for re-use. Moreover, after withdrawal of the needle into the cylinder, the plunger can again be moved in the chamber so that the slanted (misaligned) needle will contact a wall of the cylinder and be bent or destroyed within the cylinder.

While U.S. Pat. No. 4,804,370 discloses specific structure both for capturing the needle for withdrawal thereof into the chamber and for destroying the needle in the chamber, the described structure (including the offset configuration of the flexible legs forming the needle capturing receptacle) is complex, and increases manufacturing costs.

Accordingly, it is still desired to provide a hypodermic injection device wherein the needle can be withdrawn into the reservoir chamber after use, which device and needle structure is relatively simple and can be manufactured inexpensively. It is particularly desired to provide a hypodermic injection device wherein the needle structure for the device can be simply and inexpensively manufactured, without sacrificing effectiveness of the structure for reliably capturing and retracting the needle into the hypodermic reservoir chamber. Moreover, it is also desired to provide such a hypodermic injection device, wherein the needle can be withdrawn into the reservoir chamber and prevented from being moved out of the reservoir chamber into a position for re-use, with simple structure that is easily and inexpensively manufactured. It is also desired to provide a hypodermic injection device having a retractable needle, wherein, prior to use, accidental retraction of the needle into the reservoir chamber can be avoided.

SUMMARY OF THE INVENTION

Accordingly, it is an object of the present invention to provide a hypodermic injection device wherein the needle can be withdrawn into the chamber after use, so as to extract and sheath the needle in the reservoir chamber after use, the hypodermic injection device, including the needle, having a simple structure and being easily manufactured.

It is a further object of the present invention to provide a hypodermic injection device having a needle which can be withdrawn into the reservoir chamber after use, wherein the plunger of the hypodermic injection device includes structure, for capturing the needle, which is relatively simple and can be easily and inexpensively manufactured.

It is a still further object of the present invention to provide a hypodermic injection device, wherein the needle can be withdrawn into the reservoir chamber after use, and wherein the needle can be prevented from re-emerging from the reservoir chamber for re-use without the necessity of complex structures for avoiding such re-use.

It is a further object of the present invention to provide a hypodermic injection device wherein the needle can be retracted into the reservoir chamber after use, which device also includes structure to prevent accidental engagement of the needle with the needle capturing means, in order to ensure that the needle is not captured by the needle capturing means and withdrawn into the reservoir chamber prior to use.

It is a further object of the present invention to provide a hypodermic injection device, having a simplified needle structure, and wherein the retention of the needle end in the needle-retention chamber, including bending the needle end so that it can be retained in the needle-retention chamber, is simplified.

The present invention achieves the foregoing objectives by providing resilient (e.g., spring) means at the end of the needle that is internal to the reservoir chamber, so that the resilient means can enter a needle-retention chamber in the plunger and be retained therein, in or after use of the hypodermic injection device for injection, whereby the needle can then be retracted back into the reservoir chamber. The resilient means can, preferably, be a bent end of the needle, bent in such a way (and with the bent end being sufficiently flexible and resilient) to enter the needle-retention chamber in the plunger and be retained therein.

The foregoing objects are also achieved by providing a needle which cooperates with the needle-retention chamber such that an end of the needle can enter the needle-retention chamber during use of the hypodermic injection device, and such end of the needle entering the needle-retention chamber is sufficiently bent by contact with the needle-retention chamber walls so as to be retained in the chamber when the plunger is withdrawn into the reservoir chamber, whereby the needle is also withdrawn into the reservoir chamber.

The foregoing objects are also achieved by forming the plunger of two parts, each extending axially within the reservoir chamber, with one of the two parts having the needle-retention chamber in the end thereof closest to the needle. The part having the needle-retention chamber can be positioned such that it is prevented from moving toward the resilient portion of the needle structure, prior to use of the hypodermic injection device, so as to avoid capturing of the needle prior to use of the injection device.

The present invention also achieves the above objectives by providing the needle with a slight bend, so that when the needle is withdrawn into the reservoir chamber it will automatically be mis-aligned with the hole through which it has just been withdrawn, so that it cannot be extended back out of such hole for re-use.

Thus, according to the present invention, a simplified needle structure of the hypodermic injection device is provided, by providing an injection device wherein the needle can be effectively retracted into the reservoir chamber after use; and wherein re-use of the injection device can be avoided, utilizing simple structure of the needle-retaining means in, e.g., the end of the plunger and of the needle. Moreover, by the present invention accidental retraction of the needle into the reservoir chamber, prior to use of the injection device, can be avoided.

BRIEF DESCRIPTION OF THE DRAWINGS

FIG. 1b shows a detailed view of the needle and support shown in FIG. 1a;

FIGS. 6a and 6b illustrate a third embodiment of the present invention, with FIG. 6b being a cross-sectional view along line A—A of FIG. 6a;

DETAILED DESCRIPTION OF THE INVENTION

While the invention will be described in connection with specific and preferred embodiments, it is not intended to limit the invention to those embodiments. On the contrary, it is intended that the present invention cover all alterations, modifications and equivalents as may be included within the sphere and scope of the invention as defined by the appended claims.

The present invention contemplates a hypodermic injection device having a reservoir chamber for holding the injectable material, the reservoir chamber having a plunger therein for causing the reservoir chamber to be emptied during the injection, the plunger having a needle-retention chamber at the end thereof. The needle-retention chamber can include a gasket having a hole extending up into a needle-retention chamber (the needle-retention chamber being larger in cross-section than the hole extending into the needle-retention chamber). In any event, a passageway for the needle into the needle-retention chamber has a smaller cross-section than that of the needle-retention chamber. The needle structure itself has a resilient means at the end thereof within the reservoir chamber of the injection device. The resilient means has a larger dimension than the hole (passageway) extending up into the needle-retention chamber. Upon depressing the plunger so as to inject material contained in the reservoir chamber into, for example, a person, and continuing to depress the plunger, the resilient end of the needle can enter the needle-retention chamber through the hole in the gasket and, e.g., the resilient end can spring back so as to be retained within the needle-retention chamber. Thereafter, upon withdrawal of the plunger, the needle is extracted into the reservoir chamber so as to be sheathed and prevent accidental punctures by the needle.

The present invention also contemplates structure wherein the needle is slightly bent such that, when the needle is extracted into the reservoir chamber, such slight bending misaligns the needle with the hole through which the needle is extended outside of the reservoir chamber, so as to prevent reuse of the needle.

The present invention also contemplates use of plunger structure, including first and second parts axially extending in the reservoir chamber, with one of the two parts having the needle-retention chamber, the part having the needle-retention chamber not moving prior to use whereby possible accidental depression of the plunger portion containing the needle-retention chamber, and corresponding retention of the needle in the needle-retention chamber (e.g., prior to use of the injection device), can be avoided.

The present invention also contemplates additional structure wherein the needle-retention chamber itself is utilized to bend the end of the needle so as to cause the needle to be retained within the needle-retention chamber, whereby the needle can then be withdrawn into the reservoir chamber and sheathed, so as to achieve the objectives of the present invention.

In the following paragraphs, specific embodiments of the present invention will be discussed, particularly with reference to the accompanying figures. In the accompanying figures, the same reference characters are used in each of the figures to represent the same structure.

FIGS. 1a, 1b, 2 and 3 illustrate a first embodiment of the present invention.

Figure 1A:
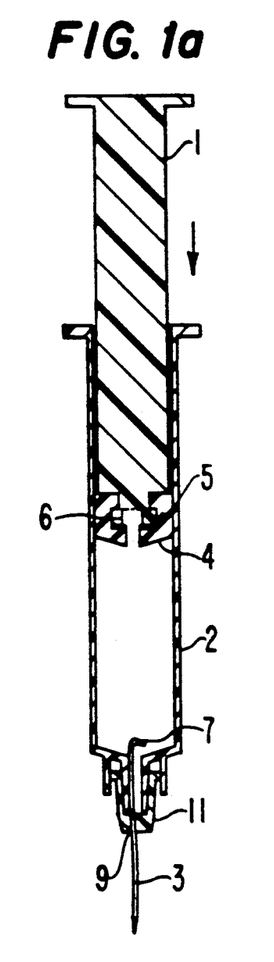
FIG. 1a illustrates a first embodiment of the hypodermic injection device according to the present invention, illustrating the needle in position to be used for injection and the plunger in a position withdrawn from the reservoir.
Figure 1B:
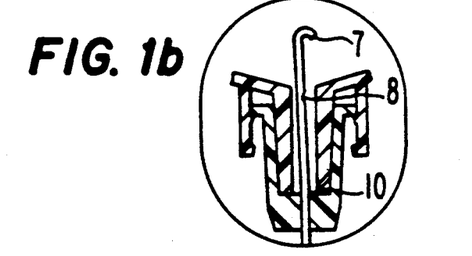

Illustratively, the hypodermic injection device shown in FIG. 1a includes a plunger 1 which is slidingly provided within a reservoir chamber 2. The plunger 1 includes, at the end thereof closest to the needle, a gasket means 4 which opens up into a needle-retention chamber 6. Also included in the needle-retaining chamber, on a lip formed by the gasket means 4, is a washer 5. The washer 5 preferably has an opening which is smaller than the opening through the gasket means 4. The gasket means 4, and washer 5, provide an opening for entry of the resilient portion of the needle. As shown in FIGS. 1a and 1b, the needle 3 has resilient means (e.g., a bent end 7, in the shape of an inverted "J", internal to the reservoir chamber 2). Also shown in FIG. 1a is needle support 11, which in a preferred embodiment is replaceable.

Instead of, or in addition to, washer 5, a membrane through which the resilient end of the needle can pierce can be used. Illustratively, in this aspect of the present invention, the membrane is provided across the opening in the gasket 4. Upon depressing the plunger a sufficient distance, the resilient end of the needle pierces the membrane and enters the needle-retention chamber. The membrane can include, e.g., scored portions having a memory, whereby after the needle (resilient means) pierces the membrane the membrane portions spring back so as to capture the end of the needle in the needle-retention chamber. By use of the membrane, entry of injectable fluid into the needle-retention chamber, prior to the needle end piercing the membrane, can be avoided.

Desirably, the resilient means extends into the reservoir chamber 2 a distance such that, when the gasket means 4 just contacts the end of the reservoir chamber 2 (such that the injectable fluid is emptied from the reservoir chamber 2) the needle is not captured in the needle-retention chamber. Preferably, the resilient means is then captured in the needle-retention chamber by further depressing the plunger so as to compress the gasket means 4 such that the resilient means then enters the needle-retention chamber. This position of the resilient means in the reservoir chamber, relative to the needle-retention chamber, can help prevent accidental engagement of the resilient means in the needle-retention chamber.

The washer 5 and/or gasket means 4 (and/or the membrane) must be sufficiently rigid so as to retain the needle within the needle-retention chamber during withdrawal of the plunger toward the top of the reservoir chamber after use of the syringe. Due to the resiliency of the end portion of the needle structure, in this first embodiment, resiliency of the structure surrounding the opening to the needle-retaining chamber is not a critical criteria. Of course, a combination of the resilient means and the structure surrounding the opening to the needle-retaining chamber must be sufficiently resilient such that the needle structure can enter the needle-retention chamber and yet be sufficiently rigid such that the needle be retained therein upon withdrawal of the plunger from the reservoir chamber.

Another method of achieving capture of the needle in the needle-retention chamber is to allow a close fit between the resilient means 7 and the hole through the gasket means 4, with the resilient means 7 being slightly offset from the hole through gasket means 4. In operation, upon depressing the plunger 1 the resilient means 7 bends as it enters the hole in the gasket means 4, because of its offset. Upon entering the needle-retention chamber, the resilient means 7 springs back and is captured in the needle-retention chamber.

The needle support 11 includes a sealing sleeve portion 9, through which the needle extends. The sealing sleeve portion 9 can be lined with any of numerous materials, such as, for example, paraffin, which allows for the immobilization of the needle during puncturing a container containing the injectable material in filling the reservoir chamber, and during puncturing of the skin, but which will give way when retraction of the needle into the reservoir chamber is desired. Alternatively, slight undersizing of the sealing sleeve means 9 will produce a press fit around the needle, thus sealing and retaining the needle in the needle support 11. The sealing sleeve means 9 should be sized so as to permit the needle to penetrate the fluid-containing bottles and skin, without axial movement of the needle, while allowing easy withdrawal of the needle for disposal after use. As another alternative, an O-ring can be provided between the needle and needle support so as to seal and retain the needle in the needle support 11.

As known conventionally in the art, the needle support can be replaceably positioned on the reservoir chamber, thereby enabling use of multiple needle sizes while utilizing the same reservoir chamber and plunger assembly. In connection with the replaceably positioned needle support, attention is directed to the teachings of U.S. Pat. No. 4,838,870, the contents of which are incorporated herein by reference in their entirety.

The needle includes a needle barrier 10 (see FIG. 1b), which prevents the needle from sliding in the needle support 11, for example, when withdrawing the needle from the container containing the material to be or withdrawing the needle from the skin. Such needle barrier 10 may be formed by bending the needle slightly, thus preventing it from sliding down the sleeve support. The needle can be provided with an S-bend, where the needle passes through needle support 11, in order to prevent the needle from sliding. Depending on the adhesion of the sealing sleeve portion 9, such needle barrier 10 may not be necessary.

In operation, the needle of the device illustrated in FIGS. 1a, 1b, 2 and 3 is inserted into a container containing, for example, a medicine to be injected. The reservoir chamber 2 is then filled by withdrawing the plunger, which creates a vacuum within the reservoir chamber so as to cause the medicine to flow up through the cavity of the needle and fill the reservoir chamber. Upon completion of the filling operation, the needle of the device of FIG. 1 is withdrawn from the container, and the skin is punctured by the needle 3 and the plunger 2 depressed, thereby injecting the fluid.

Figure 2:
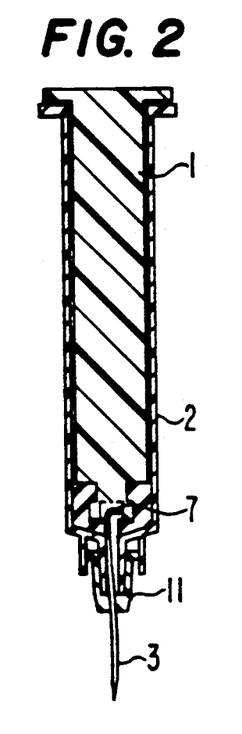
FIG. 2 illustrates the first embodiment, with the plunger extended into the reservoir and having captured the needle in the needle-retention chamber thereof.

When the plunger reaches the bottom of its stroke, the resilient means 7 enters through the hole in the gasket 4 (see FIG. 2). At the point that the resilient means 7 enters the washer 5, the spring becomes compressed in order to fit through the smaller diameter of the washer 5. After the resilient means passes through the washer, it springs back to its original shape, thereby locking it into the needle-retention chamber 6. At this point, the needle 3 can be withdrawn into the reservoir chamber (that is, extracted and sheathed in the reservoir chamber) by withdrawing the plunger 1 from the reservoir chamber. As discussed previously, the resilient means can be positioned relative to the needle-retention chamber such that the resilient means does not enter, and is not captured, in the needle-retention chamber until the gasket material is compressed, so as to help prevent accidental capture of the needle.

The resilient means can be formed in numerous shapes and angles, other than the inverted J-shape shown in the first embodiment. For example, the resilient means can be formed in a circle; an open oval; or it can be formed at any angle greater than 90°. As seen in the first embodiment, the resilient means illustratively is a bent end of the needle (e.g., formed by bending the end of the needle).

Figure 3:
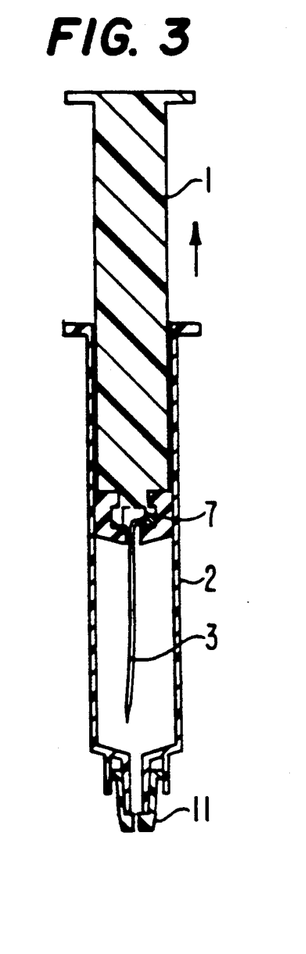
FIG. 3 illustrates the first embodiment, with the plunger withdrawn up in the reservoir chamber and the needle withdrawn into the reservoir chamber.
Figure 4A:
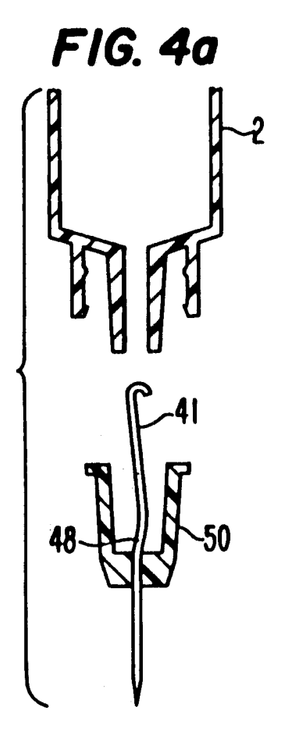
FIGS. 4a–4d. illustrate various embodiments of replaceable needle and support structures.
Figure 4B:
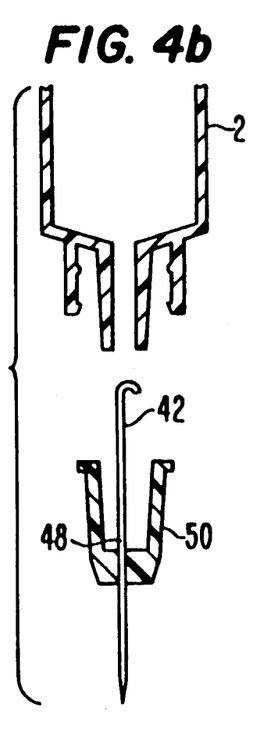
Figure 4C:
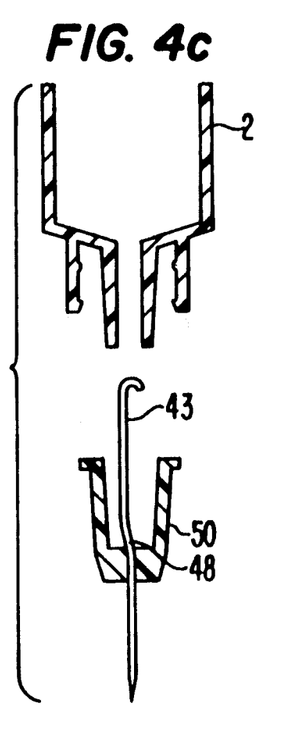
Figure 4D:
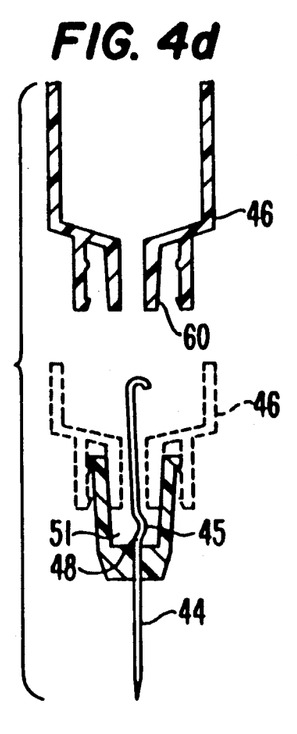

Upon withdrawal of the plunger 1 from the reservoir chamber, the needle 3 is pulled free of the support 11 and becomes safely sheathed inside the reservoir chamber 2 (see FIG. 3).

By slightly bending the needle 3, as shown in FIG. 3, the needle can be prevented from re-emerging even if the plunger is again depressed into the reservoir chamber, thereby ensuring that the needle cannot harm anyone or be re-used.

While the foregoing description has discussed use of a washer 5 for retaining the needle in the needle-retention chamber, use of such washer is merely illustrative, and not limiting of the present invention. Various other means can be utilized for retaining the needle in the needle-retaining chamber. For example, a lip could be formed on the main plunger body 1, or a molding or lip could be formed on the gasket means 4.

FIG. 2 shows a device after the needle has been captured within the needle-retaining chamber by the needle engagement system (that is, e.g., the gasket and washer openings, with at least the washer opening being sufficiently small so as to compress the resilient means).

FIG. 3 illustrates the retention of the needle 3, and also demonstrates that by slightly bending the needle 3, the needle 3 can be prevented from re-emerging from the reservoir chamber should the plunger be depressed thereafter.

FIG. 1b illustrates additional structure of the needle, including a hole 8 formed in the side of the needle to ensure flow of the fluid to be injected through the needle, should the radius of the bend providing the resilient means, at the end of the needle, prevent adequate flow of fluid to be injected.

FIG. 4 shows various configurations of needles, each being part of the present invention. Thus, FIG. 4a shows needle 41 embedded in needle support 50. The needle 41 has a right-hand bend, and has an aperture 48 near where the needle extends through the needle support 50 to outside of the needle support. FIG. 4b is similar to FIG. 4a, but the needle 42 does not have a bend. FIG. 4c shows a needle 43 with a left-hand bend. As discussed previously, the bends in the needle are utilized to prevent the needle from sliding in the needle support when the needle is removed from the fluid container or from the skin. In addition, the bends also prevent the needle from sliding in the needle support when the plunger is pushed onto the needle so as to engage the needle engagement system with the needle. The device in FIG. 4d illustrates a cavity created by the tapered nozzle means 60 of the reservoir chamber 46 and the needle holding means 50. In addition, FIG. 4d shows the needle 44 with a U-bend 45 in the middle thereof, which U-bend is sufficiently large to prevent movement of the needle in either direction during normal handling. When the needle engagement system has grasped the resilient means and retained such resilient means within the needle-retention chamber, upward pressure caused by withdrawal of the plunger straightens the bend 45 slightly, permitting the needle to pass through the nozzle means 60 and into the main portion of the reservoir chamber.

Figure 5:
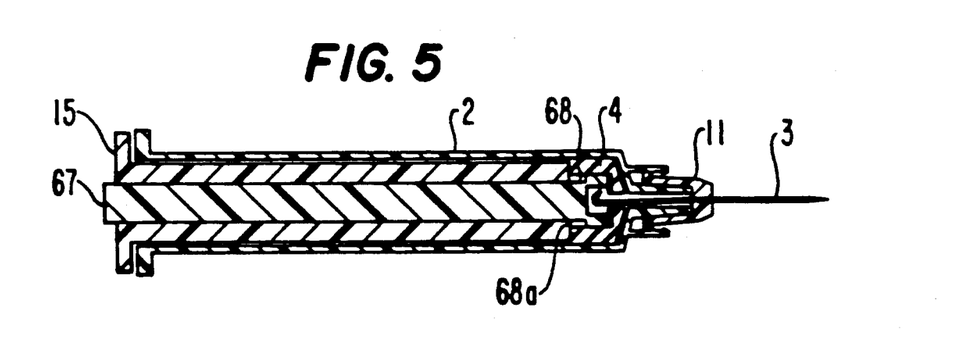
FIG. 5 illustrates a second embodiment of the present invention.

A second embodiment of the hypodermic injection device according to the present invention is shown in FIG. 5. This figure illustrates a hypodermic device which allows for the extraction and sheathing of the needle after use, but also provides structure which prevents accidental engagement of the needle engagement system with the needle, prior to use of the injection device.

Specifically, the structure of FIG. 5 includes an axially extending portion of the plunger, represented by reference character 67 in FIG. 5, which prevents accidental engagement of the needle engagement system with the needle. The gasket means 4 includes an extending hollow portion 68 whereby the rod 67 and its attached needle engagement system, including the needle-retention chamber, are axially slidable within the gasket means 4 and plunger 15. In a shipping and handling mode, the needle engagement system is in an upper position (not shown). In this upper position, where the, e.g., member forming the needle-retention chamber is in contact with an upper shoulder 68a of extending hollow portion 68, the resilient means 7 is not captured in the needle engagement system (that is, not retained in the needle-retention chamber), and the needle engagement system is out of reach of the needle. In use of this second embodiment, the needle is inserted into a container containing the liquid to be injected, and the plunger is withdrawn, causing a vacuum to form which pulls the rod 67 into a position where the needle engagement system can engage the needle. Then, when an injection is being given, the thumb of the user depresses the rod 67 along with the plunger 15. This keeps the needle engagement system extended during contact with a needle.

Figure 6A:
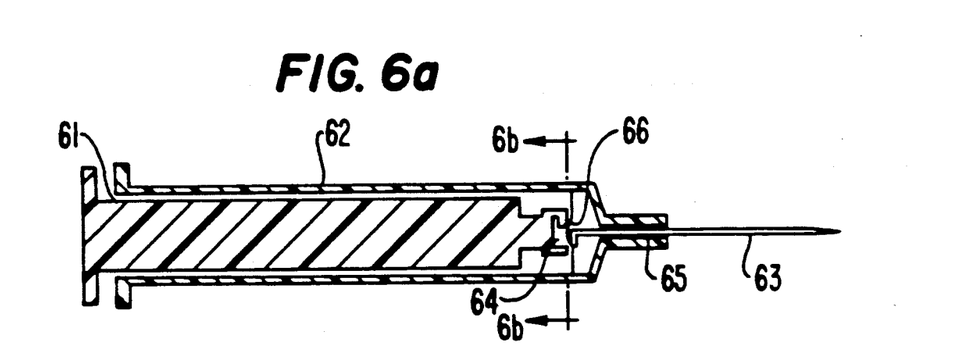
Figure 6B:
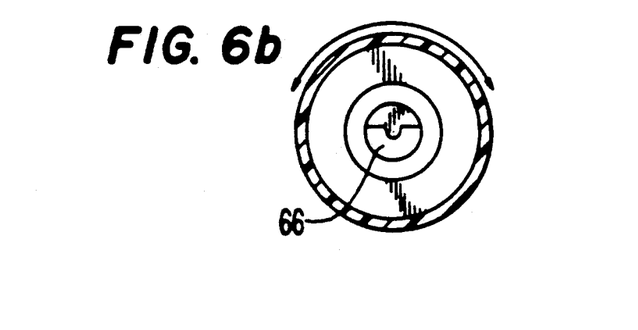

FIGS. 6a and 6b illustrate another embodiment of the present invention, for extracting and sheathing the needle in the reservoir chamber. In this embodiment, the needle 63 is bent at an angle, such as, for example, 90°. The needle-retaining chamber is so configured that the indent portion of the needle can extend into the needle-retaining chamber substantially without contacting the chamber. The needle-retaining chamber is so proportioned such that, upon turning the plunger, the needle-retaining chamber will engage the angled portion of the needle behind an outcropping within the chamber 64. This embodiment operates in that, upon getting the injection, the angled portion extends into the cavity 66 of the needle-retaining chamber 64. Then, in order to engage the needle, the plunger 62 is twisted so as to position the angled portion of needle 63 behind the outcropping inside the chamber 64. At this point, the plunger can be withdrawn, breaking the needle 63 free of the sealing means 65, and pulling the needle safely inside the reservoir chamber 62.

Figure 7A:
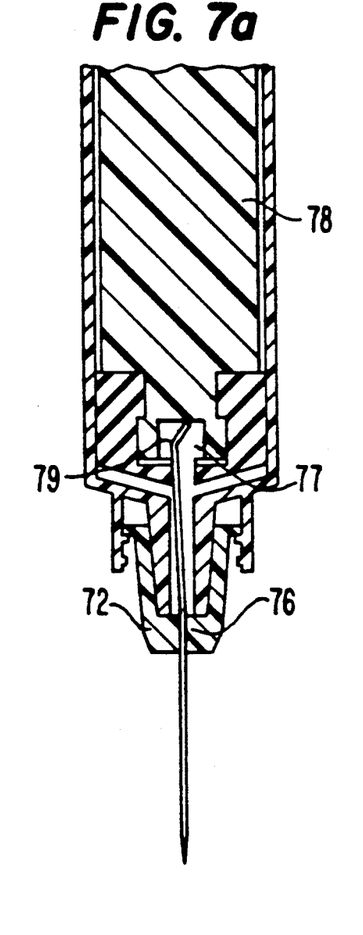
FIGS. 7a and 7b illustrate a fourth embodiment of the present invention, with FIG. 7a showing the plunger partially extended into the reservoir and FIG. 7b showing the plunger substantially fully extended into the reservoir chamber.
Figure 7B:
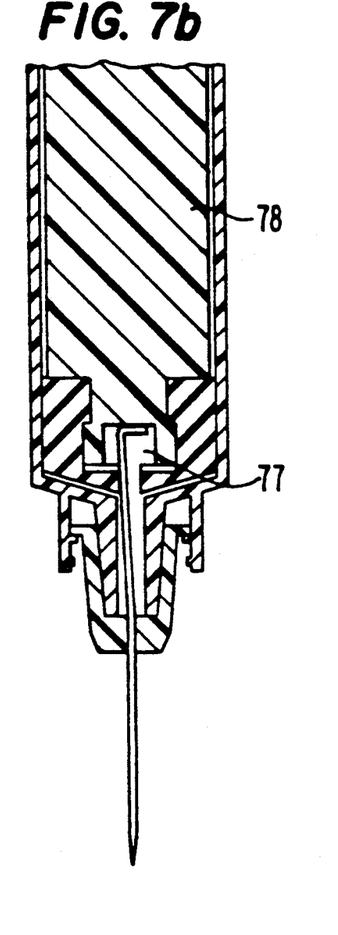

FIGS. 7a and 7b illustrate a further embodiment of the present invention, for extracting and sheathing the needle. In this embodiment, the end portion of the needle in the interior of the reservoir chamber is slightly bent. The entrance to the needle-retention chamber 77 is slightly larger than the dimensions required by the bent end portion of the needle for entering the chamber 77; moreover, the needle, in its bent condition, extends sufficiently into the reservoir chamber such that when the plunger 78 reaches the bottom of its stroke, the bent needle contacts the top of the needle-retention chamber such that contact with the wall of the needle-retention chamber further bends the end of the needle. Bent over further in this fashion, the end of the needle, as bent, is larger than the opening into the needle-retention chamber. When the plunger is withdrawn, the needle, the end portion of which is retained in the needle-retention chamber, is pulled free of the sealing means 76 through the needle support member 72.

While FIGS. 7a and 7b show the top of the needle-retaining chamber 77 to be substantially perpendicular to the direction that the needle extends, thereby bending the end of the needle to a 90° angle, the top of the chamber 77 can be at an angle other than perpendicular to the needle. This would form the further bend in the end portion of the needle into an angle other than 90°, such as, for example, 45°. This would give the needle a better engagement in the needle-retention chamber, and would improve reliability of retraction of the needle into the reservoir chamber.

Figures 8A, 8B:
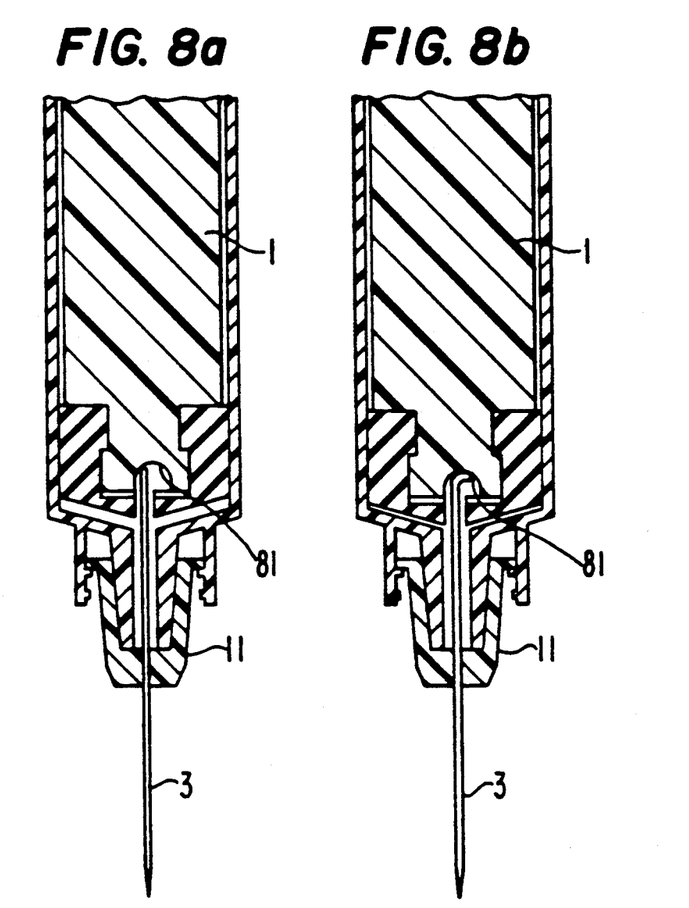
FIGS. 8a and 8b illustrate a fifth embodiment of the present invention, with FIG. 8a showing the plunger partially extended into the reservoir chamber and FIG. 8b showing the plunger substantially fully extended into the reservoir chamber.

FIGS. 8a and 8b illustrate a further embodiment of the present invention. The device shown in FIGS. 8a and 8b functions similarly to the device shown in FIGS. 7a and 7b, but uses a needle-retaining cavity with a curved top 81 to bend the end portion of the needle (or to further bend a bent end portion of the needle). As is clear in FIG. 8a, by using a chamber having a curved top a straight needle (with no bend originally at the interior end portion thereof) can be utilized, with the curved top of the needle-retention chamber providing sufficient bend in the needle so that the end portion of the needle will be retained in the plunger from the reservoir chamber.

Figure 9A:
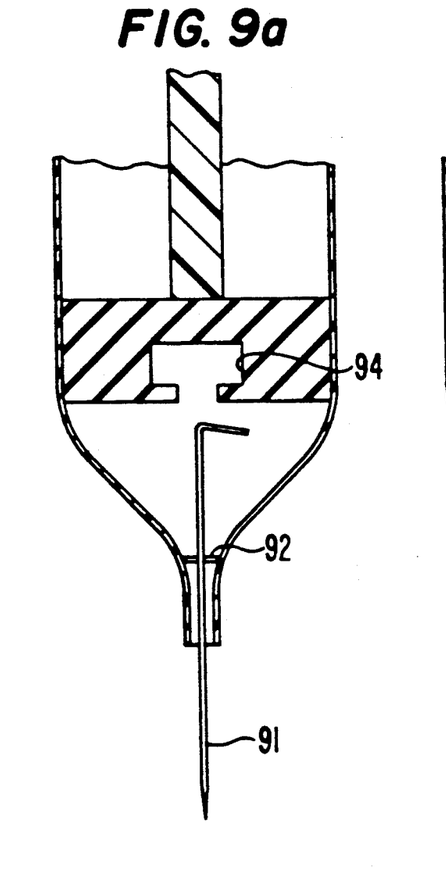
FIGS. 9a and 9b illustrate a sixth embodiment of the present invention, with FIG. 9a showing the plunger partially extended into the reservoir chamber and FIG. 9b showing the plunger substantially fully extended into the reservoir chamber.
Figure 9B:
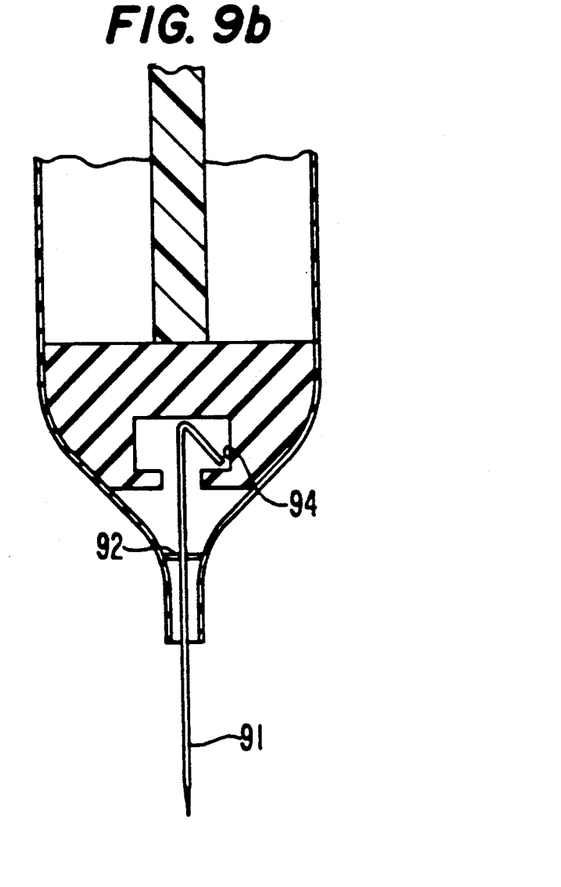

FIGS. 9a and 9b show a still further embodiment according to the present invention. In this embodiment, the needle 91, which can be bent in any of a wide variety of angles but which is preferably bent at about a 90° angle, is bent further when the plunger is depressed to its lowest position and the needle is extended into the needle-retaining chamber 94, due to the bent portion of the needle being larger than the opening into the needle-retaining chamber 94. When the bent portion of the needle 91 passes the lip and enters the cavity, it rebounds back towards its original angle, to a limited extent, as shown in FIG. 9b. FIGS. 9a and 9b also show needle barrier 92, which may be disk-shaped or may be a bend in the needle, to prevent the needle from sliding in the needle support during engagement of the needle with the needle engagement system, culminating in the bent end of the needle being positioned in the needle-retaining chamber.

Figure 10:
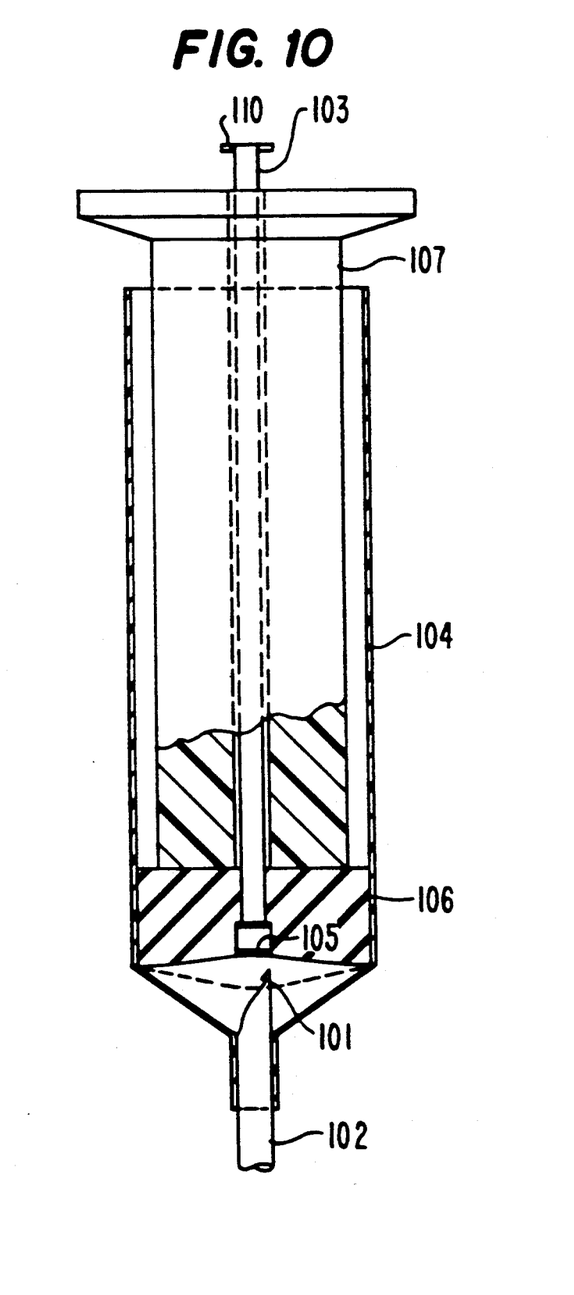
FIGS. 10 and 11 respectively illustrate seventh and eighth embodiments of the hypodermic injection device according to the present invention.

FIG. 10 illustrates another embodiment of the present invention, for sheathing the needle of the hypodermic syringe after use. In this embodiment, the needle has a bard hook 101 at its interior end. Moreover, a rod 103 traverses the interior of plunger 107, in the axial direction. In operation, the needle is positioned in such a manner as to prevent accidental impalement of the bard hook on the rod 103 during normal handling and storage. In use of the syringe of FIG. 10, the needle 102 punctures a fluid container, containing the fluid to be injected, and the plunger 107 is then withdrawn so as to create a vacuum in the interior of reservoir chamber 104. This causes the fluid from the fluid bottle to flow into the reservoir chamber, and also causes the rod 103 to be pulled down. The rod 103 is prevented from being sucked into the reservoir chamber by lip 110. After the needle has penetrated the skin, the plunger is depressed, injecting the fluid as desired. The thumb of the user can also be used to depress the rod 103 together with the plunger 107, allowing the bard hook 101 to penetrate the needle adhesion member 105 at the bottom of the plunger stroke. The needle can then be withdrawn from the sealing means by withdrawing the plunger from the reservoir chamber, safely sheathing the needle within the reservoir chamber.

Figure 11:
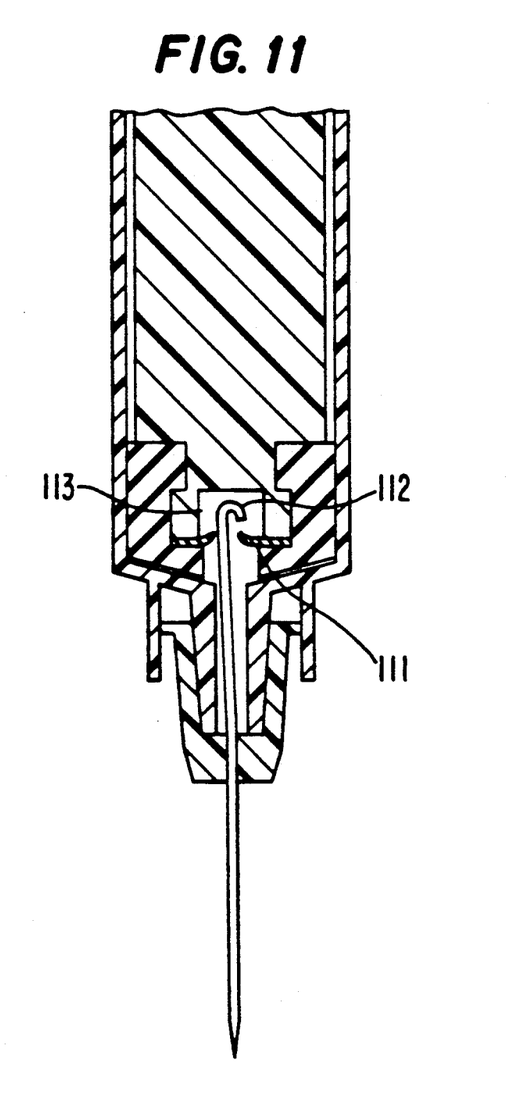

FIG. 11 shows a further embodiment of the present invention. The structure shown in FIG. 11 works in the same manner as in the first embodiment, wherein the resilient means 112 is captured within the needle-retention chamber 113. The structure of FIG. 11 includes an opening into the needle-retaining chamber that is surrounded by a funnel-shaped structure 111. Such funnel-shaped structure facilitates capture of the needle within the needle-retention chamber, guiding the resilient means of the needle structure to the opening into the needle-retaining chamber.

Figures 12A, 12B, 12C:
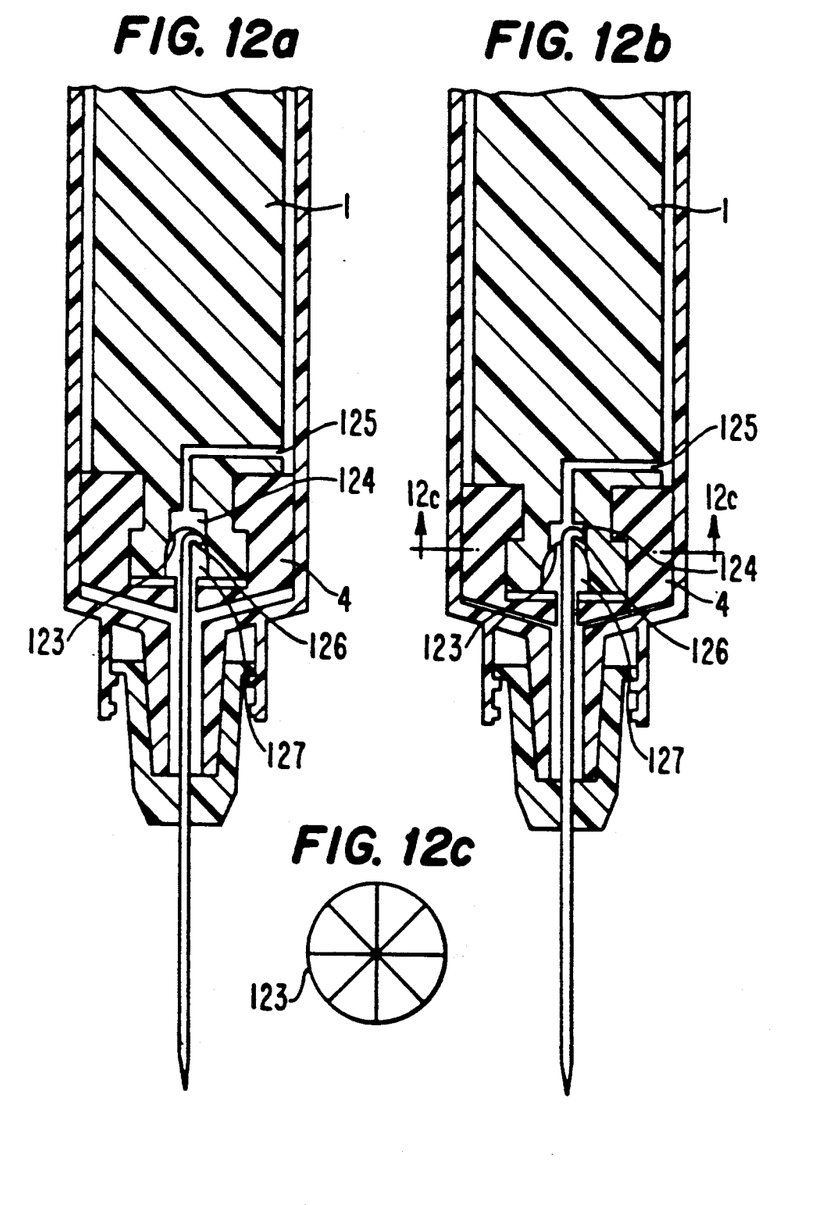
FIGS. 12a–12c illustrate a ninth embodiment of the present invention, with FIG. 12a showing the plunger partially extended into the reservoir chamber, FIG. 12b showing the plunger substantially fully extended into the reservoir chamber, and FIG. 12c being a cross-sectional view along line A—A of FIG. 12b.

FIGS. 12a, 12b and 12c show a further embodiment of the present invention. This embodiment includes a rupturable roof 123 of cavity 127. For example, such rupturable roof can include a scored portion of the roof of chamber 127, as shown in FIG. 12c. The roof 123 of the chamber 127 is airtight prior to penetration of the roof by the needle, permitting normal use of the hypodermic syringe.

When the plunger 1 is depressed, the bent portion at the end of the needle (shown as reference character 126 in FIG. 12a) forces open the rupturable roof 123. After the end portion 126 passes through the rupturable roof 123, the roof portions spring back, surrounding the needle and trapping the end portion. The needle can then be withdrawn upon withdrawing the plunger 1 from the reservoir chamber.

This embodiment shown in FIGS. 12a, b and c also includes a chamber 124, into which the end of the needle passes upon forcing open the rupturable roof 123, and a channel 125 which extends through the plunger 1 above the gasket means 4 so as to substantially be exposed to the atmosphere. Accordingly, through use of the chamber 124 and channel 125, when the rupturable roof 123 has been penetrated by the end portion of the needle air can then pass through the channel 125, thereby breaking the vacuum formed upon withdrawal of the plunger from the reservoir chamber after use of the injection device. This facilitates withdrawal of the plunger.

The hypodermic injection devices according to the present invention can be made of materials conventionally used for forming hypodermic syringes. For example, various plastics, metals, glass and gasket materials (e.g., rubber) can be used in forming the needle support, reservoir chamber and plunger. In addition, the needle can be made of conventional materials (e.g., metal or plastics), insofar as such materials have the requisite flexibility in providing the resilient means of the needle, particularly wherein such resilient means is an integral part of the needle (formed, e.g., by bending an end of the needle). Moreover, the hypodermic injection device according to the present invention can be made by techniques commonly used in forming such devices, including molding and/or extruding techniques.

Thus, according to the present invention, a hypodermic syringe having a retractable needle can easily be provided, utilizing a relatively simple needle, and a relatively simple plunger structure, that does not add any substantial cost to the final device. Moreover, the hypodermic injection device according to the present invention can avoid accidental and/or improper relocation of the needle after retraction of the needle into the reservoir chamber, and also avoids accidental retraction of the needle into the reservoir chamber.

While I have shown and described several embodiments in accordance with the present invention, it is understood that the same is not limited thereto, but is susceptible of numerous changes and modifications as are known to one having ordinary skill in the art, and I therefor do not wish to be limited to the details shown and described herein, but intend to cover all such modifications as are encompassed by the scope of the appended claims.

What is claimed is:

1. A hypodermic injection device comprising:
   a reservoir chamber having two ends, the reservoir chamber being adapted to hold material to be injected;
   a needle structure extending out from a first end of the reservoir chamber, the needle structure including a first end within the reservoir chamber and a second end outside the reservoir chamber, said needle structure extending through a hole in the first end of the reservoir chamber; and
   a plunger extending into the reservoir chamber from a second end of the reservoir chamber and slidably mounted into the reservoir chamber so as to cause the reservoir chamber to be emptied of injectable material through said needle structure when the plunger is moved in the reservoir chamber toward the needle structure,
   wherein said plunger includes a needle-retention chamber in an end portion thereof closest to the needle structure, and the first end of the needle structure includes resilient means adapted to be inserted in and retained in the needle-retention chamber when the plunger is moved toward the needle structure, the resilient means being sufficiently resilient such that the resilient means is compressed when entering the needle-retention chamber so as to be retained therein, the needle-retention chamber being sufficiently rigid so as to retain the resilient means therein when withdrawing the plunger from the reservoir chamber, whereby the needle structure can be retracted into the reservoir chamber after the resilient means has been retained in the needle-retaining chamber and the plunger has been withdrawn from the reservoir chamber.

2. A hypodermic injection device according to claim 1, wherein said needle structure is a needle, the resilient means being a bent end portion of the needle, said bent end portion being bent to have a sufficient width across the bend such that the bent end portion must be compressed to be inserted in the needle-retention chamber.

3. A hypodermic injection device according to claim 2, wherein said bent end portion is a portion bent in an inverted J-shape.

4. A hypodermic injection device according to claim 2, wherein the plunger includes a gasketing member as said end portion, with said needle-retaining chamber having an entrance thereto through said gasketing member.

5. A hypodermic injection device according to claim 4, wherein said gasketing member has a restricted opening at the end of the plunger, through which the resilient means of the needle structure can enter the needle-retention chamber, with a washer member, having a smaller opening than the size of the restricted opening, being provided on the gasketing member and providing an entry to the needle-retention chamber, whereby the resilient means enters the needle-retention chamber through the restricted opening and the opening in the washer member.

6. A hypodermic injection device according to claim 2, wherein said needle structure is bent such that, when the needle structure is retracted into the reservoir chamber, the needle structure is not aligned with said hole in the first end of the reservoir chamber and cannot pass through said hole in the event that the plunger is depressed into the reservoir chamber.

7. A hypodermic injection device according to claim 4, wherein the resilient means of the needle structure extends to a location in the reservoir chamber such that when the plunger is depressed so as to contact an end of the reservoir chamber the resilient means is not retained in the needle-retention chamber, and upon further depressing the plunger so as to compress gasketing material of the gasketing member the resilient means can enter and be retained in the needle-retention chamber.

8. A hypodermic injection device according to claim 1, wherein said needle structure is bent such that, when the needle structure is retracted into the reservoir chamber, the needle structure is not aligned with said hole in the first end of the reservoir chamber and cannot pass through said hole in the event that the plunger is depressed into the reservoir chamber.

9. A hypodermic injection device according to claim 1, wherein the needle structure includes a needle support in which the needle is mounted, the needle extending out of the reservoir chamber and out of the needle support, the needle support being replaceably mounted on the first end of the reservoir chamber.

10. A hypodermic injection device according to claim 9, wherein the first end of the reservoir chamber includes a mounting structure for replaceably mounting the needle support, the mounting structure being adapted to mount needle supports having different sizes of needles, whereby a single reservoir chamber can be used with different sizes of needles.

11. A hypodermic injection device according to claim 1, wherein the needle structure includes a needle barrier means for preventing the needle structure from sliding in a direction out of the first end of the reservoir chamber.

12. A hypodermic injection device according to claim 11, wherein said needle barrier means is constituted by a bend in the needle structure.

13. A hypodermic injection device according to claim 1, wherein said needle structure includes a hollow needle having a hole in the side thereof, in flow communication with the reservoir chamber, to enable injectable material in the reservoir chamber to enter the hollow needle through the hole in the side of the needle.

14. A hypodermic injection device according to claim 1, wherein the needle-retention chamber includes a lip member forming an opening to the needle-retention member, through which the resilient means enters the needle-retention chamber, the lip member having a funnel shape so as to facilitate entry of the resilient means into the needle-retention chamber.

15. A hypodermic injection device according to claim 1, wherein the resilient means of the needle structure extends to a location in the reservoir chamber such that when the plunger is depressed so as to contact an end of the reservoir chamber to empty the reservoir chamber the resilient means is not retained in the needle-retention chamber, and upon further depressing the plunger so as to compress the plunger the resilient means can enter and be retained in the needle-retention chamber.

16. A hypodermic injection device according to claim 1, wherein the plunger includes first and second parts, each axially extending in the reservoir chamber, said first part having said needle-retention chamber, the second part being movable axially toward the needle structure independent of movement of the first part.

17. A hypodermic injection device according to claim 1, wherein the resilient means, and a remaining part of the needle structure, is made of a single member.

18. A hypodermic injection device according to claim 17, wherein the entire needle structure, including the resilient means, is made of the single member.

19. A hypodermic injection device according to claim 1, wherein the plunger further includes a membrane provided across an opening to the needle-retention chamber, the resilient means piercing the membrane when entering the needle-retention chamber.

20. A hypodermic injection device according to claim 19, wherein said membrane has scored portions having a memory, whereby after the resilient means pierces the membrane the scored portions spring back so as to retain the resilient means in the needle-retention chamber.

21. A hypodermic injection device according to claim 1, wherein the resilient means is slightly offset from an opening to the needle-retention chamber such that the resilient means bends as it enters the opening into the needle-retention chamber, and, upon entering the needle-retention chamber springs back so as to be retained in the needle-retention chamber.

22. A hypodermic injection device comprising:
a reservoir chamber having two ends, the reservoir chamber being adapted to hold material to be injected;
a needle structure extending out from a first end of the reservoir chamber, the needle structure including a first end within the reservoir chamber and a second end outside the reservoir chamber, said needle structure extending through a hole in the first end of the reservoir chamber; and
a plunger extending into the reservoir chamber from a second end of the reservoir chamber and slidably mounted into the reservoir chamber so as to cause the reservoir chamber to be emptied of injectable material through said needle structure when the plunger is moved in the reservoir chamber toward the needle structure, wherein said plunger includes a needle-retention chamber in an end portion thereof closest to the needle structure, said needle-retention chamber including a first part forming an opening to the chamber and a second part forming a main body of the chamber, a cross-section of the opening being smaller than a cross-section of the main body, wherein the first end of the needle structure includes resilient means adapted to be retained in the main body of the needle-retention chamber when the plunger is moved toward the needle structure, and wherein the cross-section of said opening is sufficiently smaller than the resilient means, and the cross-section of the main body is sufficiently large, such that when the plunger is moved toward the needle structure the resilient means is compressed and upon entering the main body springs back and is captured in the needle-retention chamber, and said first part is sufficiently rigid such that the resilient means is retained in the needle-retention chamber when withdrawing the plunger from the reservoir chamber, whereby the needle structure can be retracted into the reservoir chamber after the resilient means has been retained in the needle-retention chamber and the plunger has been withdrawn from the reservoir chamber.

* * * * *